United States Patent [19]
Schweighofer et al.

[11] Patent Number: 6,123,658
[45] Date of Patent: Sep. 26, 2000

[54] MAGNETIC STIMULATION DEVICE

[75] Inventors: Peter Schweighofer, Nuremberg; Michael Moritz, Misieleau; Franz Schmitt, Erlangen, all of Germany

[73] Assignee: Siemens Aktiengesellschaft, Munich, Germany

[21] Appl. No.: 09/313,559

[22] Filed: May 14, 1999

[30] Foreign Application Priority Data

May 15, 1998 [DE] Germany .......................... 198 22 019

[51] Int. Cl.$^7$ .................................................. A61N 1/00
[52] U.S. Cl. .................................................................. 600/13
[58] Field of Search ..................................... 600/9, 13, 14

[56] References Cited

U.S. PATENT DOCUMENTS

| | | |
|---|---|---|
| 1,610,863 | 12/1926 | Kucher . |
| 4,866,749 | 9/1989 | Uematu ................................... 378/134 |
| 5,086,442 | 2/1992 | Gemmel et al. ........................ 378/132 |
| 5,743,844 | 4/1998 | Tepper et al. ............................. 600/14 |
| 5,766,124 | 6/1998 | Polson ...................................... 600/13 |

FOREIGN PATENT DOCUMENTS

| | | |
|---|---|---|
| 0 182 160 | 5/1986 | European Pat. Off. . |
| 336 781 | 7/1919 | Germany . |
| 27 27 907 | 1/1979 | Germany . |
| 36 07 235 | 9/1987 | Germany . |
| 41 32 428 | 4/1993 | Germany . |

OTHER PUBLICATIONS

"Neuro–und Sinnes–Physiologie," Schmidt, E.d (1995), Chapters 2 and 3.

"Development, Optimization and Testing Of New Devices For Magnetomotive Nerve Fibre Stimulation," Schmid et al, Biomet, Technik, vol. 38, No. 12 (1993), pp. 317–324.

*Primary Examiner*—Max Hindenburg
*Attorney, Agent, or Firm*—Hill & Simpson

[57] ABSTRACT

A magnetic stimulation device has at least one stimulation coil, which is connected with its terminals to the output of at least one controllable electronic power converter and which has an inductance and current and voltage carrying capability, so that the stimulation pulses it generates permeate at least one volume on the order of magnitude of limbs, head or trunk of a patient. The controllable electronic power converter contains at least one activatable and deactivatable power semiconductor switch with short switching times. The electronic power converter is connected with its input to a voltage intermediate circuit. The voltage intermediate circuit and the controllable electronic power converter have a layout for high output voltages and currents, so that action potentials can be triggered even in deeper neuromuscular tissue of a patient, and the magnetic stimulation device offers wide freedom in the selection of the stimulation pulse shapes.

10 Claims, 1 Drawing Sheet

MAGNETIC STIMULATION DEVICE

BACKGROUND OF THE INVENTION

1. Field of the Invention

The present invention relates to a neuromuscular magnetic stimulation device.

2. Description of the Prior Art

In the field of medical diagnosis and therapy, magnetic stimulation devices serve for the magnetic stimulation of nerve fibers and muscular tissue. Compared to electrical stimulation by means of stimulating current, an advantage of magnetic impulse stimulation is the low amount of pain associated with the stimulation, since higher current densities do not arise in the region of the pain receptors of the skin. Another advantage of magnetic stimulation is the greater penetration ability, it being possible to excite deeper tissue as well, particularly deeper nerve fibers.

The book "Neuro- and Sinnesphysiologie" (R. F. Schmidt, pub., $2^{nd}$ ed, 1995: chapters 2 and 3) contains a detailed description of neurophysiological processes. The nervous system coordinates the activities of the various organs and reactions of the body to the environment, for example. This occurs primarily by an alteration of the potential of nerve cells. All cells have a resting potential. At the resting potential, all membrane currents of a cell exist in balance. If the potential is depolarized by an additional membrane current, which enters the cell by means of an external influence, for example, this is associated with a potential variation, known as an action potential. This depolarizing membrane current is also called stimulation. The triggering potential for an action potential is called the threshold. At the threshold, the balance of the membrane currents changes. For a short time, additional membrane currents arise which depolarize the membrane. This state is also called excitation. An action potential is associated with an action.

For example, every contraction of a muscle fiber is accompanied by an action potential in the muscle fiber, and every reaction of a sensory cell to a sensory stimulus is transmitted by action potentials.

European Application 0 182 160 teaches a device for generating electromagnetic impulses with a semi-circular shape, which serves particularly for the promotion of the microcirculation of blood in the region of the hair roots and the skin, for example, to counteract hair loss. To this end, a diode rectifier bridge is connected to an alternating voltage transformer in a Graetz circuit which supplies a coil that generates pulses.

German OS 36 07 235 teaches a device for generating unipolar air ions and electromagnetic pulse fields for reducing human reaction time while simultaneously increasing attentiveness. To generate the electromagnetic impulse fields, a frequency generator with a decoupling amplifier connected downstream, and a coil which generates the pulse field, are connected to a voltage source.

German OS 41 32 428 teaches a magnetotherapy device for magnetotherapeutic treatment. To generate a pulsed magnetic field, an unstable multivibrator is connected to a battery, this multi-vibrator feeding two cylindrical coils with iron cores. The device is constructed as a pocket device.

U.S. Pat. No. 5,743,844 teaches a device for therapy by means of pulsing electromagnetic fields for the promotion of the healing of bone and body tissues, particularly in the form of a battery-powered device which can be carried on the body. A coil which generates the magnetic field is supplied from two voltage sources of different voltage levels via a specific circuit which contains two field effect transistors and two capacitors as basic elements. This circuit thus has a fixed pulse-pause time ratio.

The devices described in the above referenced patents are all designed such that the magnetic pulse fields, or alternating fields, which they generate act on the human body below the threshold for triggering action potentials. The effects in the human body that can be so achieved part very diffuse and scientifically controversial. Magnetic stimulation devices which purposefully trigger action potentials, particularly in deeper neuromuscular tissue, are another category of devices altogether. Not only is the use and therapeutic effect of these devices different, but also the electrical powers to be applied for this purpose are many times greater, which is exhibited in correspondingly high current and voltage values. Due to their overall low-voltage and low-current design, the devices described in the above referenced patents are not suited to this purpose.

A magnetic stimulation device for triggering action potentials even in deeper neuromuscular tissue is described in the essay "Entwicklung, Optimierung and Erprobung neuer Geräte für die magnetomotorische Stimulation von Nervenfasern," (M. Schmid, T. Weyh and B. -U. Meyer, Biomedizinische Technik 38,1993:317–324). This device has a stimulation coil which, together with a high-voltage capacitor, forms a parallel resonant circuit, i.e. which functions as a resonant circuit. The high-voltage capacitor is charged by a controllable network part and thereby accumulates the necessary pulse energy for the emission of a stimulation impulse. For this purpose the controllable network part is connected to the high-voltage capacitor with the terminals used for charging.

A thyristor is inserted, as an electronic switch, into the circuit of the high-voltage capacitor, which closes via the stimulation coil. While the high-voltage capacitor is charged by the controllable network part in preparation for the pulse emission, the thyristor remains open, and the parallel resonant circuit is interrupted. When the charge voltage reaches the value desired by the user, a charging switch belonging to the charging connection disconnects the high-voltage capacitor from the controllable network part, and the stimulation pulse is triggered by a firing of the thyristor. The high-voltage capacitor discharges via the stimulation coil. When the high-voltage capacitor has been completely discharged, the direction of the energy flow reverses. It would now be possible for the high-voltage capacitor to be charged with a reversed polarity, but this is avoided by an unbiased circuit branch arranged parallel to the high-voltage capacitor as an additional current path.

The unbiased branch contained an unbiased diode and a resistor connected in series with this diode.

In the unbiased branch, the energy ring-down from the stimulation coil is largely absorbed. The unbiased diode assures that the unbiased branch takes over the current only when the recovery (negative polarity energy flow) from the stimulation coil replaces the positive polarity discharging process of the high-voltage capacitor (commutation). Ultimately, the high-voltage capacitor, which nevertheless is slightly charged given reversed polarity, also delivers its energy to the resistor.

The resonant frequency of the parallel resonant circuit formed by the stimulation coil and the high-voltage capacitor is determined by the selection of the capacitance of the high-voltage capacitor and the inductance of the stimulation coil, and lies in the range of 1 to 3 kHz. If the capacitance of the high-voltage capacitor is varied, then the resonant frequency of the parallel resonant circuit and thus the rate of the current rise in the stimulation coil can be changed. The stimulation intensity is determined by the initial voltage at the high-voltage capacitor. As an additional parameter, the repetition rate, which lies in the region of about 10 Hz, can also be set.

German OS 196 07 704 also teaches a device for the magnetic excitation of neuromuscular tissue. The known device has an excitation coil (stimulation coil) which, together with a storage capacitor (high-voltage capacitor), forms a parallel resonant circuit, i.e. which likewise functions as a resonant circuit. In this device also, only resonant frequencies in the range of 1 to 3 kz can be realized.

SUMMARY OF THE INVENTION

An object of the present invention is to provide magnetic stimulation device for triggering action potentials even in deeper neuromuscular tissue, which device offers greater freedom in the selection of the stimulation pulse shapes.

This object is achieved in an inventive magnetic stimulation device having at least one stimulation coil, which is connected with its terminals to the output of at least one controllable electronic power converter and which has an inductance as well as current carrying capacity and voltage carrying capacity, so that the stimulation pulses it generates permeate at least one volume on the order of magnitude of the limbs, head or trunk of a patient, whereby the controllable electronic power converter having at least one activable and deactivable power semiconductor switch with short switching times. The controllable electronic power converter is connected with its input to a voltage intermediate circuit, and the voltage intermediate circuit and the controllable electronic power converter are laid out (designed and dimensioned) for high output voltages and currents, so that action potentials can be triggered in deeper neuromuscular tissue of a patient.

The term "short switching time" refers to switching times of about 1 μs or less in the inventive magnetic stimulation device.

In the magnetic stimulation device, the stimulation coil is supplied with the required pulse energy via a voltage intermediate circuit and a controllable electronic power converter. The inventive magnetic stimulation device thus does not function as a resonant circuit in which the stimulation coil and a high-voltage capacitor form a parallel resonant circuit.

Greater freedom in the selection of the stimulation pulse shape can be achieved with the use of activable and deactivable power semiconductor switches, since resonant operation can be avoided. Controllable network parts with specific charging connections can be forgone.

In an embodiment of the inventive magnetic stimulation device, the voltage intermediate circuit contains a capacitor that is charged by a network part. The network part need not be controllable and is preferably implemented as a high-voltage network part. Separate charging switches are then forgone. In contrast to the high-voltage capacitor of the known magnetic stimulation devices, the intermediate circuit capacitor is not discharged completely and thus dies not determine any time characteristics for the stimulation pulses. The intermediate circuit capacitor thus can be implemented with considerably higher capacitance. The shapes of the stimulation pulses generated by the stimulation coil are controlled only by the repetition rate and the pulse period of the activation phases of the activatable and deactivatable power semiconductor switches.

Since, in contrast to comparable magnetic stimulation devices in the prior art, the stimulation coil is not a part of a parallel resonant circuit, additional degrees of freedom result from the selection of the inductance of the stimulation coil.

In the framework of the invention, the controllable electronic power converter can be implemented as a unipolar electronic power converter, preferably as a chopper or as a bipolar electronic power converter, preferably as an inverter.

The activatable and deactivatable power semiconductor switches must have short switching times, and so transistors, particularly IGBTs or MOSFETs are currently preferably utilized for this purpose.

DESCRIPTION OF THE PREFERRED EMBODIMENTS

Figure 1:
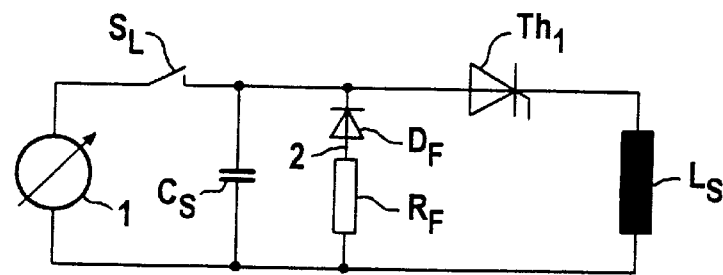
FIG. 1 shows a magnetic stimulation device according to the prior art.

In FIG. 1, a stimulation coil $L_S$ forms a parallel resonant circuit with a high-voltage capacitor $C_S$. The high-voltage capacitor $C_S$ is charged by a controllable network part 1 and thereby accumulates the necessary pulse energy for the delivery of a stimulation pulse. To this end, the controllable network part 1 is connected with terminals for charging to the high-voltage capacitor $C_S$. Of the charging connection of the controllable network part 1, only the charging switch $S_L$ is depicted.

A thyristor $Th_1$ is inserted, as an electronic switch, into the circuit of the high-voltage capacitor $C_S$ which closes via the stimulation coil $L_S$. While the high-voltage capacitor $C_S$ is charged by the controllable network part 1 in preparation for the pulse delivery, the thyristor $Th_1$ remains open, and the parallel resonant circuit is interrupted. When the charging voltage has reached the value desired by the user, the charging switch $S_L$ disconnects the high-voltage capacitor $C_S$ from the controllable network part 1, and the stimulation pulse is triggered by the firing of the thyristor $Th_1$. The high-voltage capacitor discharges via the stimulation coil $L_S$. When the high-voltage capacitor has discharged completely, the direction of the energy flow reverses. A possible charging of the high-voltage capacitor $C_S$. with reversed polarity by providing an unbiased branch 2 in parallel with the high-voltage capacitor $C_S$ as an additional current path.

The unbiased branch 2 contains an unbiased diode $D_F$ and a resistor $R_F$ connected in series.

In the unbiased branch 2, the ring-down from the stimulation coil $L_S$ is largely absorbed. The unbiased diode $D_F$ assures that the unbiased branch 2 only takes up the current when the recovery from the stimulation coil $L_S$ replaces the discharge process of the high-voltage capacitor $C_S$ (commutation). Ultimately, the high-voltage capacitor $C_S$, which is slightly charged given reversed polarity, also delivers its energy to the resistor $R_F$.

In the magnetic stimulation device according to the prior art as depicted in FIG. 1, the resonant frequency of the parallel resonant circuit that is formed by the stimulation coil $L_S$ and the high-voltage capacitor $C_S$ is determined by the selection of the capacitance of the high-voltage capacitor $C_S$ and the inductance of the stimulation coil $L_S$, and it lies in the range between 1 and 3 kHz. If the capacitance of the high-voltage capacitor $C_S$ is varied, then the resonant frequency of the parallel resonant circuit, and thus the rate of the current rise in the stimulation coil $L_S$, can be altered. The stimulation intensity is determined by the initial voltage at the high-voltage capacitor $C_S$. The repetition rate, which lies in the region of about 10 Hz, can also be adjusted as an additional parameter.

Figure 2:
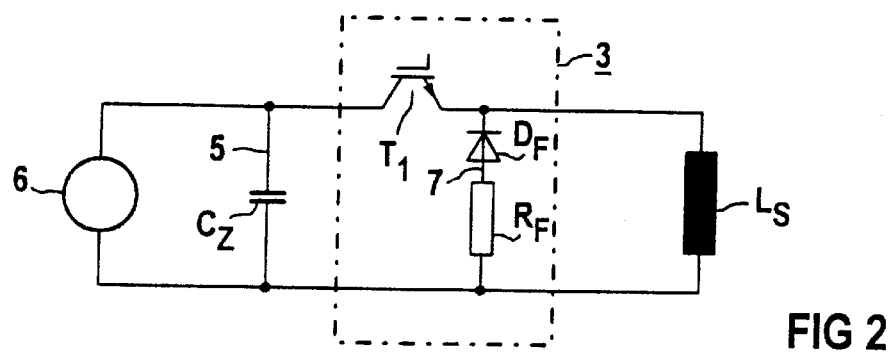
FIG. 2 shows a first embodiment of a magnetic stimulation device according to the invention.
Figure 3:
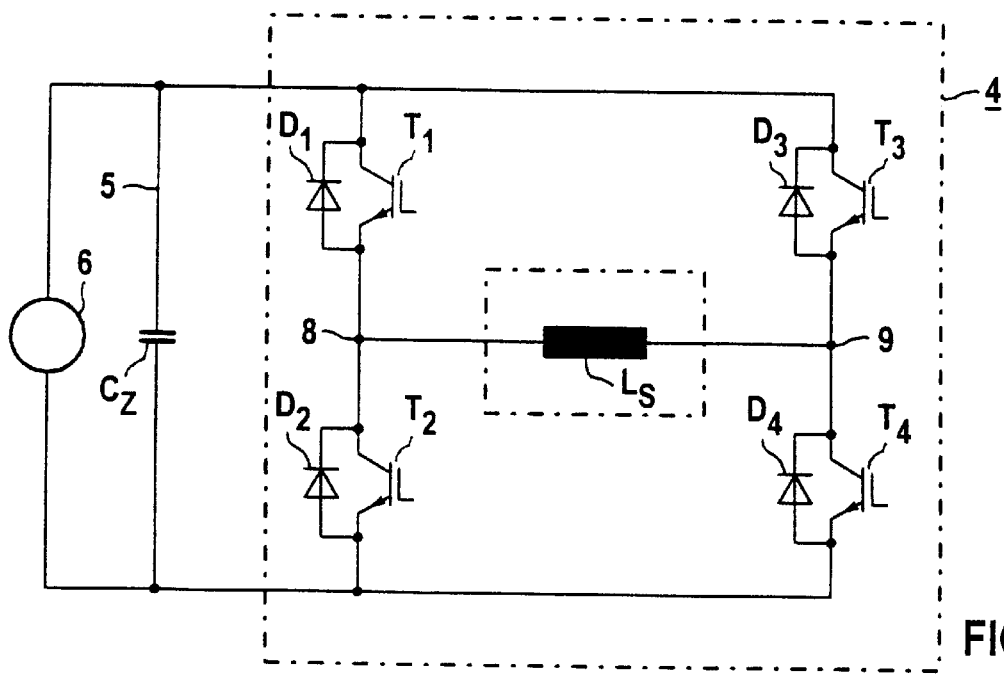
FIG. 3 shows a second embodiment of an inventive magnetic stimulation device.

The inventive magnetic stimulation device, as shown in the exemplary embodiments of FIGS. 2 and 3, respectively, has at least one stimulation coil $L_S$, which is connected with its terminals to the output of at least one controllable electronic power converter 3 (FIG. 2), or to at least one controllable electronic power converter 4 (FIG. 3).

In the framework of the invention, the controllable electronic power converter can be implemented as a unipolar electronic power converter (electronic power converter 3 in FIG. 2) or as a bipolar electronic power converter (electronic power converter 4 in FIG. 3).

The electronic power converters 3 and 4 each contain at least one activatable and deactivatable power semiconductor switch $T_1$ with short switching times. In an embodiment of the invention, the activatable and deactivatable power semiconductor switches are implemented as transistors. Each power electronic converter 3 and 4 is connected with its input to a voltage intermediate circuit 5. The voltage intermediate circuit 5 contains at least one intermediate circuit capacitor $C_Z$. The intermediate circuit capacitor $C_Z$ is charged by a network part 6, which need not be controllable and which is preferably a high-voltage network part.

In the magnetic stimulation device depicted in FIG. 2, the stimulation coil $L_S$ is charged with the energy stored in the intermediate circuit capacitor $C_Z$ subsequent to the activation of the transistor $T_1$, and a unipolar stimulation pulse is thus triggered. Subsequent to the deactivation of the transistor $T_1$, the current flowing in the stimulation coil $L_S$ is dismantled via an unbiased branch 7 arranged in the unipolar electronic power converter 3. At least one unbiased diode $D_F$ is arranged in the unbiased branch 7. In the exemplary embodiment, in the unbiased arm 7 a resistor $R_F$ is connected in series with the unbiased diode $D_F$. The resistor $R_F$ determines the time constant and can be forgone if the parasitic resistances in the circuit are sufficiently large.

In the magnetic stimulation device depicted in FIG. 3, the electronic power converter 4 is implemented as a full bridge and thus as a bipolar electronic power converter, i.e., with two bridge branches. The first bridge branch is formed by the transistors $T_1$ and $T_2$ and the second bridge branch is formed by the transistors $T_3$ and $T_4$. The stimulation coil $L_S$ is connected with its first terminal to the central tap point 8 of the first bridge branch and with its second terminal to the central tap point 9 of the second bridge branch. With respect to the intermediate circuit 5 and its intermediate circuit capacitor $C_Z$, the statements made with reference to the magnetic stimulation device depicted in FIG. 2 apply.

Unbiased diodes $D_1$ to $D_4$ are respectively connected in parallel with the transistors $T_1$ to $T_4$. Either the unbiased diodes $D_1$ to $D_4$ can be implemented as separate (discrete) diodes, or they can be part of the relevant transistors $T_1$ to $T_4$ as parasitic diodes.

The bipolar electronic power converter 4 generates positive output voltages on the basis of the activation of the transistors $T_1$ to $T_4$. Negative output voltages are generated by the activation of the transistors $T_2$ and $T_3$.

Specific charging switches $S_L$, which are required in the magnetic stimulation device according to the prior art (FIG. 1), are forgone in the inventive magnetic stimulation device. Unlike the high-voltage capacitor $C_S$ (FIG. 1), the intermediate circuit capacitor $C_Z$ is no longer completely discharged and no longer determines any time characteristics for the stimulation impulses. Therefore, the intermediate circuit capacitor $C_Z$ can be implemented with significantly higher capacitance. The shapes of the stimulation pulses which are generated by the stimulation coil $L_S$ are controlled only via the repetition rate and the pulse period of the activation phases of the transistor $T_1$ (FIG. 2), or respectively, of the transistors $T_1$ to $T_4$ (FIG. 3).

Since, in contrast to the magnetic stimulation device depicted in FIG. 1, the stimulation coil $L_S$ is not a part of a parallel resonant circuit, in the inventive magnetic stimulation device additional degrees of freedom result by means of the selection of the inductance of the stimulation coil $L_S$.

To achieve the required carrying capacity of the switch, the activatable and deactivatable power semiconductor switch elements, which are illustrated here as individual components, can also be implemented as parallel and/or series connections of a plurality of transistors and/or IGBTs and/or MOSFETs.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic stimulation device comprising:
   at least one stimulation coil having an inductance and a current carrying capacity and a voltage carrying capacity, and having coil terminals;
   a controllable power converter having an output connected to said coil terminals, said controllable power converter containing at least one activatable and deactivatable power semiconductor switch with a short switching time, said controllable power converter having an input;
   an intermediate voltage circuit connected to said input of said controllable power converter, said voltage intermediate circuit and said controllable power converter containing, in combination, circuitry for producing high output voltages and currents at said coil terminals for operating said stimulation coil to generate stimulation pulses which permeate an approximate volume selected from the volumes consisting of a human limb volume, a human head volume and human trunk volume, with a selectable magnetic field intensity for triggering action potentials in deep neuromuscular tissue in said approximate volume.

2. A magnetic stimulation device as claimed in claim 1 wherein said controllable power converter comprises a unipolar power converter.

3. A magnetic stimulation device as claimed in claim 2 wherein said unipolar power converter comprises a chopper.

4. A magnetic stimulation device as claimed in claim 1 wherein said controllable power converter comprises a bipolar power converter.

5. A magnetic stimulation device as claimed in claim 4 wherein said bipolar power converter comprises an inverter.

6. A magnetic stimulation device as claimed in claim 4 wherein said bipolar power converter comprises a full-bridge circuit.

7. A magnetic stimulation device as claimed in claim 4 wherein said bipolar power converter comprises a half-bridge circuit.